US00PP08918P

United States Patent [19]

Saville

[11] Patent Number: Plant 8,918

[45] Date of Patent: Oct. 4, 1994

[54] MINIATURE ROSE PLANT NAMED SAVALIGHTS

[75] Inventor: F. Harmon Saville, Rowley, Mass.

[73] Assignee: Nor'East Miniature Roses, Inc., Rowley, Mass.

[21] Appl. No.: 147,816

[22] Filed: Nov. 4, 1993

[51] Int. Cl.[5] ..... A01H 5/00

[52] U.S. Cl. ..... Plt./7.1

[58] Field of Search ..... Plt. 7.1, 10

*Primary Examiner*—Howard J. Locker

*Attorney, Agent, or Firm*—Christie, Parker & Hale

[57] ABSTRACT

A new miniature rose with red and yellow bicolor flowers.

1 Drawing Sheet

SUMMARY OF THE INVENTION

The present invention relates to a new and distinct variety of rose plant of the miniature rose class, which was created by me by crossing as seed parent an unnamed, unpatented seedling of my creation, and as pollen parent the variety known as 'Party Girl' (U.S. Plant Pat. No. 4,598). The varietal denomination of this new rose is 'Savalights'.

Among the novel characteristics possessed by this new variety which distinguishes it from its parents and all other varieties of which I am aware is its attractive yellow flowers edged with red.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—Unnamed seedling.

*Pollen parent.*—'Party Girl' (U.S. Plant Pat. No. 4,598).

Class: Miniature.

The following observations are made of specimens grown under glass in Essex County, Mass., during the month of September.

FLOWER

Blooming habit: Recurrent, continuous.

A. Bud:

(1) *Size.*—Medium.

(2) *Form.*—Pointed.

(3) *Color.*—As sepals divide, bud color is near 8D-B edged with near 45B.

(4) *Sepals.*—Slightly longer than bud, sparsely foliated.

(5) *Peduncle.*—Length — About $\frac{3}{4}$ to $\frac{7}{8}$ inch. Aspect — Straight. Strength — Erect. Color — Near 144A.

B. Bloom:

(1) *Size.*—Average size when fully expanded — About $1\frac{1}{2}$ inches.

(2) *Borne.*—Singly and several together in small sprays.

(3) *Form.*—High centered becoming flat, petals loosely roll outward.

(4) *Petalage.*—Number of petals under normal conditions — About 30 to 35.

(5) *Color.*—During first two days, underside of inner petals at center of flower is near 12D to 12A edged with near 45B; undersurface of outer petals is near 8A edged with near 46C; base of petals at point of attachment near 12A; petal top surfaces generally remain near 45B, until blooms open and age, with yellow coloration of below about $\frac{1}{3}$ of petal length becoming visible as petals unfurl. However, where petals bunch and through about $\frac{1}{3}$ stage red coloration of top surface dominates appearance; reverse of petals tends toward near 8A and general tonality from a distance with petal undersurface visible is yellow with lacing effect of red; however, appearance from top of flower is generally red. As bloom ages the yellow color lightens to near 8C-D edged with 45D, then to 8C-D edged with 54A, then shades to 54C; the yellow lightens and the red tends to "blue," becoming magenta, and after three or more days yellow whitens still further but retains yellow tint, near 8D to 8C edged with 54A washing into 54C.

C. Petals:

(1) *Texture.*—Average.

(2) *Appearance.*—Inside velvety and outside satiny.

(3) *Form.*—Rounded fan shape, with slight point at apex.

(4) *Arrangement.*—Imbricated, regularly arranged, shingle-like.

(5) *Petaloids in center.*—Few.

(6) *Persistence.*—Drop off cleanly.

(7) *Fragrance.*—None.

(8) *Lasting quality.*—Very long on plant and as cut flower.

REPRODUCTIVE ORGANS

A. Stamens, filaments and anthers:
*Arrangement.*—Regularly arranged around styles.
*Color.*—Near 14B, Anthers — Near 10B.

B. Pollen:
*Color.*—Near 10A.

C. Styles: Even length.

D. Stigmas:
*Color.*—Near 145C.

E. Hips: None observed.

PLANT

A. Form: Upright, compact.

B. Growth: Very vigorous, uniform branching.
*Height attained.*—About 16 to 20 inches.

C. Foliage: Compound 5 to 7 leaflets.
(1) *Size.*—Medium.
(2) *Quantity.*—Abundant.
(3) *Color.*—New foliage: Upper side — Near 146A. Underside — Near 146B. Old foliage: Upper side — Near 137A. Underside — Near 137C.
(4) *Shape.*—Oval, pointed.
(5) *Texture.*—Upper side is semi-glossy; Underside is matte.
(6) *Edge.*—Serrated.
(7) *Serration.*—Serrulate.
(8) *Leaf stem.*—Color — Near 146A. Underside — 146B.
(9) *Stipules.*—Medium length, smooth.
(10) *Resistance to disease.*—Blackspot — Average. Mildew — Average. Rust — Average.

D. Wood:
(1) *New wood.*—Color — Near 138A. Bark — Smooth.
(2) *Old wood.*—Color — Near 143A. Bark — Slightly rough.

E. Thorns:
*Quantity (main stalk).*—Ordinary.
*On laterals from stalk.*—Ordinary.
*Form.*—Long, straight.
*Length.*—Medium.
*Color.*—Near 185C.
*Position.*—Irregular.
*Prickles.*—None.

I claim:

1. A new and distinct variety of rose plant of the miniature rose class, substantially as shown and described.

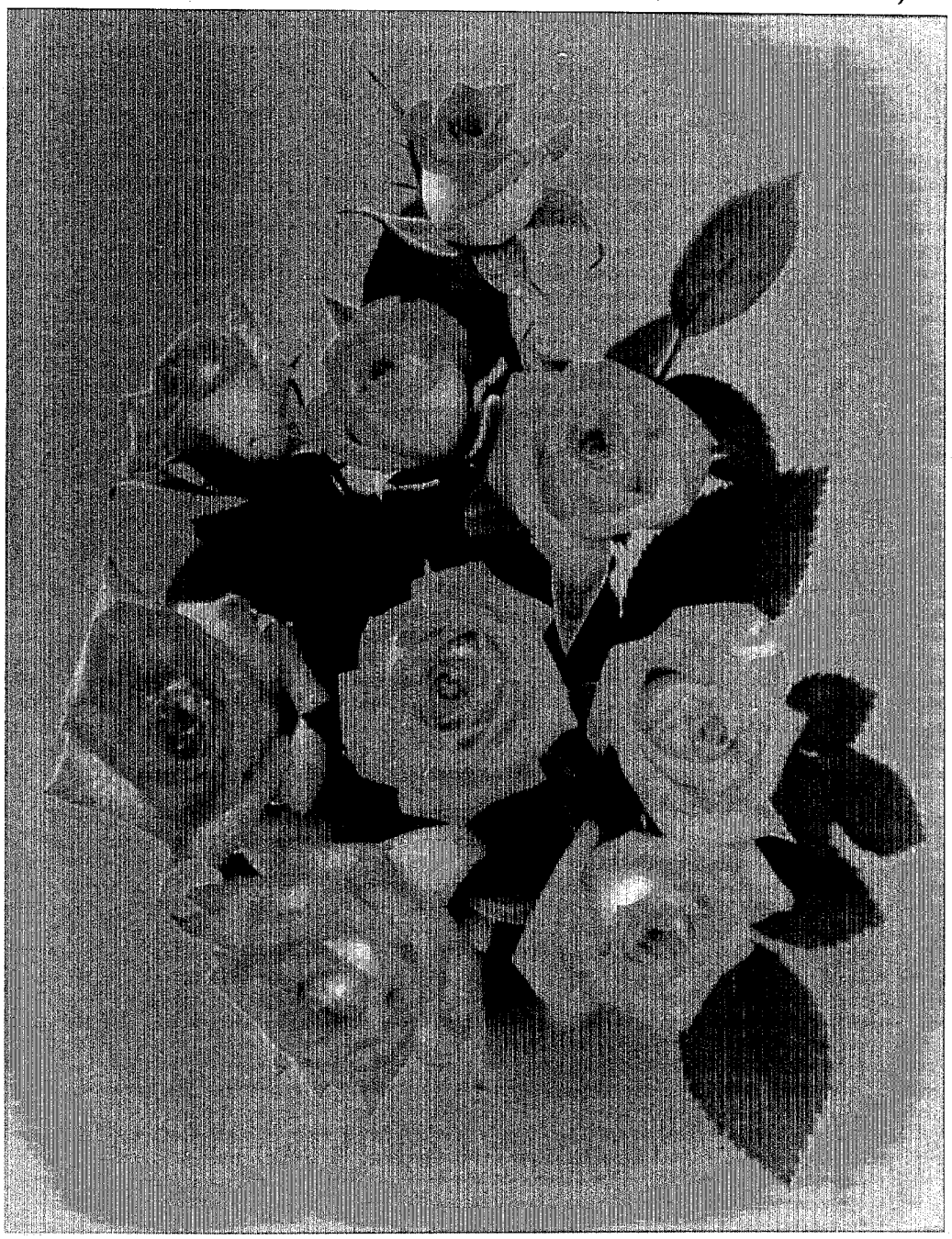

* * * * *